(12) United States Patent
Barclay et al.

(10) Patent No.: US 7,090,968 B2
(45) Date of Patent: Aug. 15, 2006

(54) COPOLYMERS HAVING NITRILE AND ALICYCLIC LEAVING GROUPS AND PHOTORESIST COMPOSITIONS COMPRISING SAME

(75) Inventors: George G. Barclay, Jefferson, MA (US); Zhibiao Mao, Shrewsbury, MA (US); Robert J. Kavanagh, Cambridge, MA (US)

(73) Assignee: Shipley Company, L.L.C., Marlborough, MA (US)

( * ) Notice: Subject to any disclaimer, the term of this patent is extended or adjusted under 35 U.S.C. 154(b) by 14 days.

(21) Appl. No.: 10/683,532

(22) Filed: Oct. 10, 2003

(65) Prior Publication Data

US 2004/0076906 A1    Apr. 22, 2004

Related U.S. Application Data

(63) Continuation of application No. 09/413,763, filed on Oct. 7, 1999, now Pat. No. 6,692,888.

(51) Int. Cl.
*G03F 7/30* (2006.01)

(52) U.S. Cl. .............. 430/326; 430/270.1; 430/905; 430/910; 526/270; 526/281; 526/282

(58) Field of Classification Search ............ 430/270.1, 430/905, 910, 326; 526/270, 281, 282
See application file for complete search history.

(56) References Cited

U.S. PATENT DOCUMENTS

| | | | |
|---|---|---|---|
| 5,212,043 A | 5/1993 | Yamamoto et al. | 430/192 |
| 5,635,332 A | 6/1997 | Nakano et al. | 430/270.1 |
| 5,968,713 A | 10/1999 | Nozaki et al. | 430/326 |
| 6,057,083 A | 5/2000 | Taylor et al. | 430/326 |
| 6,146,806 A | 11/2000 | Maeda et al. | 430/170 |
| 6,165,674 A | 12/2000 | Taylor et al. | 430/270.1 |
| 6,239,231 B1 * | 5/2001 | Fujishima et al. | 525/337 |
| 6,692,888 B1 | 2/2004 | Barclay et al. | |

FOREIGN PATENT DOCUMENTS

| | | |
|---|---|---|
| DE | 195 25 221 | 7/1995 |
| DE | 196 26 003 | 6/1996 |
| EP | 0 663 616 | 7/1995 |
| EP | 0 915 382 | 5/1999 |
| EP | 0 930 542 A1 | 7/1999 |
| EP | 0 982 628 A | 3/2000 |
| EP | 1 004 568 A | 5/2000 |
| JP | 53 081114 A | 7/1978 |
| JP | 11-171932 | 6/1999 |

OTHER PUBLICATIONS

T. Wallow et al., "New Approaches to Production-Worthy 193nm Photoresists based on Acrylic Copolymers" Proceedings of the SPIE—The International Society for Optical Engineering, vol. 3333, No. 1, Feb. 23, 1998, pp. 579-586, XP002156905.

* cited by examiner

*Primary Examiner*—John S. Chu
(74) *Attorney, Agent, or Firm*—Peter F. Coreless; Darryl P. Frickey; Edwards Angell Palmer & Dodge

(57) ABSTRACT

The present invention includes polymers and photoresist compositions that comprise the polymers as a resin binder component. Photoresists of the invention include chemically-amplified positive-acting resists that can be effectively imaged at short wavelengths such as sub-200 nm, particularly 193 nm. Polymers of the invention contain in specified molar ratios both nitrile and photoacid labile groups that have an alicyclic moiety, particularly a bridged bicyclic or tricyclic group or other caged group. Polymers and resists of the invention can exhibit substantial resistance to plasma etchants.

16 Claims, No Drawings

COPOLYMERS HAVING NITRILE AND ALICYCLIC LEAVING GROUPS AND PHOTORESIST COMPOSITIONS COMPRISING SAME

This application is a continuation of copending application Ser. No. 09/413,763 filed on Oct. 7, 1999.

BACKGROUND OF THE INVENTION

1. Field of the Invention

The present invention relates to new polymers and use of such polymers as a resin binder component for photoresist compositions, particularly chemically-amplified positive-acting resists that can be effectively imaged at short wavelengths such as sub-200 nm, particularly 193 nm. Polymers of the invention contain in specified molar ratios both nitrile and photoacid labile groups that have an alicyclic moiety, particularly a bridged bicyclic group or other caged group.

2. Background

Photoresists are photosensitive films used for transfer of images to a substrate. A coating layer of a photoresist is formed on a substrate and the photoresist layer is then exposed through a photomask to a source of activating radiation. The photomask has areas that are opaque to activating radiation and other areas that are transparent to activating radiation. Exposure to activating radiation provides a photoinduced chemical transformation of the photoresist coating to thereby transfer the pattern of the photomask to the photoresist-coated substrate. Following exposure, the photoresist is developed to provide a relief image that permits selective processing of a substrate.

A photoresist can be either positive-acting or negative-acting. For most negative-acting photoresists, those coating layer portions that are exposed to activating radiation polymerize or crosslink in a reaction between a photoactive compound and polymerizable reagents of the photoresist composition. Consequently, the exposed coating portions are rendered less soluble in a developer solution than unexposed portions. For a positive-acting photoresist, exposed portions are rendered more soluble in a developer solution while areas not exposed remain comparatively less developer soluble. Photoresist compositions are described in Deforest, Photoresist Materials and Processes, McGraw Hill Book Company, New York, ch. 2, 1975 and by Moreau, Semiconductor Lithography, Principles, Practices and Materials, Plenum Press, New York, ch. 2 and 4.

More recently, chemically-amplified-type resists have been increasingly employed, particularly for formation of sub-micron images and other high performance applications. Such photoresists may be negative-acting or positive-acting and generally include many crosslinking events (in the case of a negative-acting resist) or deprotection reactions (in the case of a positive-acting resist) per unit of photogenerated acid. In the case of positive chemically-amplified resists, certain cationic photoinitiators have been used to induce cleavage of certain "blocking" groups pendant from a photoresist binder, or cleavage of certain groups that comprise a photoresist binder backbone. See, for example, U.S. Pat. Nos. 5,075,199; 4,968,581; 4,883,740; 4,810,613; and 4,491,628, and Canadian Patent Application 2,001,384. Upon cleavage of the blocking group through exposure of a coating layer of such a resist, a polar functional group is formed, e.g., carboxyl or imide, which results in different solubility characteristics in exposed and unexposed areas of the resist coating layer. See also R. D. Allen et al., Proceedings of SPIE, 2724:334–343 (1996); and P. Trefonas et al. Proceedings of the 11th International Conference on Photopolymers (Soc. Of Plastics Engineers), pp 44–58 (Oct. 6, 1997).

While currently available photoresists are suitable for many applications, current resists also can exhibit significant shortcomings, particularly in high performance applications such as formation of highly resolved sub-half micron and sub-quarter micron features.

Consequently, interest has increased in photoresists that can be photoimaged with short wavelength radiation, including exposure radiation of about 250 nm or less, or even about 200 nm or less, such as wavelengths of about 248 nm (provided by KrF laser) or 193 nm (provided by an ArF exposure tool). See European Published Application EP915382A2. Use of such short exposure wavelengths can enable formation of smaller features. Accordingly, a photoresist that yields well-resolved images upon 248 nm or 193 nm exposure could enable formation of extremely small (e.g. sub-0.25 m) features that respond to constant industry demands for smaller dimension circuit patterns, e.g. to provide greater circuit density and enhanced device performance.

However, many current photoresists are generally designed for imaging at relatively higher wavelengths, such as G-line (436 nm) and I-line (365 mm) are generally unsuitable for imaging at short wavelengths such as sub-200 nm. Even shorter wavelength resists, such as those effective at 248 nm exposures, also are generally unsuitable for sub-200 nm exposures, such as 193 nm imaging.

More specifically, current photoresists can be highly opaque to extremely short exposure wavelengths such as 193 nm, thereby resulting in poorly resolved images.

Efforts to enhance transparency for short wavelength exposure can negatively impact other important performance properties such as substrate adhesion and resistance to etchants employed after development, which in turn can dramatically compromise image resolution. In particular, reducing aromatic (e.g. phenyl or substituted phenyl such as phenol) content of a resist to thereby increase transparency at sub-200 nm exposures can provide a resist that exhibits quite poor resistance to plasma etchants used to process substrate surfaces bared upon development.

It thus would be desirable to have new photoresist compositions, particularly resist compositions that can be imaged at short wavelengths such as sub-200 nm exposure wavelengths, particularly 193 nm. It would be particularly desirable to have such resist compositions that exhibit good transparency to sub-200 nm wavelengths, particularly 193 nm, as well as good resistance to plasma etchants

SUMMARY OF THE INVENTION

We have now found novel polymers and photoresist compositions that comprise the polymers as a resin binder component. Polymers of the invention contain repeat units of both nitrile groups and acid labile ester groups with an alicyclic moiety leaving group. The photoresist compositions of the invention can provide highly resolved relief images upon exposure to extremely short wavelengths, particularly sub-200 nm wavelengths such as 193 nm.

More particularly, polymers of the invention contain at least two distinct repeat units: 1) nitrile groups, such as may be provided upon polymerization of methacrylonitrile or acrylonitrile; and 2) photoacid labile groups that contain a tertiary ester alicyclic hydrocarbon group that has two or more fused or bridged rings. Preferred tertiary ester groups include optionally substituted fencyl groups, particularly ethyl fencyl; optionally substituted alkyl adamantyl, particularly a methyladamantyl leaving group (where the ester oxygen is linked to the tertiary carbon of the methyladamantyl moiety); optionally substituted tricyclo decanyl, and optionally substituted pinanyl. Additional alicyclic ester groups also will be suitable, including additional bicyclic, tricyclic arid other polycyclic moieties.

Moreover, we have surprisingly found that significantly enhanced lithographic performance and plasma etch resistance can be provided where the molar ratios of those units 1) and 2) are within specified values, i.e. where the polymer contains from about 20 to 50 mole percent of nitrile units 1), and from about 30 to 60 mole percent of alicyclic units 2).

Additionally, we have found that use of a photoacid labile ester group that contains a fencyl group, particularly ethylfencyl, provides a resist system that can be deprotected at relatively lower temperatures (lower activation energy required). More particularly, it has been found that resists of the invention that contain a polymer having nitrile units and photoacid labile ester units having ethylfencyl leaving groups can provide high resolution relief images (e.g. sub-quarter micron) with post-exposure bakes (ca. 60 seconds duration) of no more than 110° C., or even no more than about 100° C. or 90° C.

Polymers of the invention also may contain units in addition to groups the nitrile and alicyclic groups 1) and 2). For example, dissolution enhancers may be included in a polymer of the invention, such as anhydrides and lactones. Polymers containing at least nitrile groups 1), alicyclic ester acid labile groups 2) and lactone groups 3) are particularly preferred. Contrast enhancing groups also may be present in polymers of the invention, such as groups provided by polymermization of methacrylic acid, acrylic acid, and such acid protected as photoacid labile esters, e.g. as provided by reaction of ethoxyethyl methacrylate, t-butoxy methacrylate, t-butylmethacrylate and the like.

For use in photoresists to be imaged at 193 nm, preferably a polymer of the invention will be substantially free of any phenyl or other aromatic groups. For example, preferred polymers contain less than about 5 mole percent aromatic groups, more preferably less than about 1 mole percent aromatic groups, more preferably less than about 0.1, 0.02, 0.04 and 0.08 mole percent aromatic groups and still more preferably less than about 0.01 mole percent aromatic groups. Particularly preferred polymers are completely free of aromatic groups. Aromatic groups can be highly absorbing of sub-200 nm radiation and thus are undesirable for polymers used in photoresists imaged with such short wavelength radiation.

The invention also provides methods for forming relief images, including methods for forming a highly resolved relief image such as a pattern of lines where each line has essentially vertical sidewalls and a line width of about 0.40 microns or less, and even a width of about 0.25, 0.20 or 0.16 microns or less. The invention further provides articles of manufacture comprising substrates such as a microelectronic wafer substrate or liquid crystal display or other flat panel display substrate having coated thereon a polymer, photoresist or resist relief image of the invention.

In a further aspect, the invention includes novel compounds that are useful to prepare polymers of the invention. In particular, ethylfenchol methacrylate and ethylfenchol acrylate are provided, together with methods of synthesis of those monomers.

Other aspects of the invention are disclosed infra

DETAILED DESCRIPTION OF THE INVENTION

As stated above, polymers of the invention comprise contain repeat units of both nitrile groups and acid labile ester groups with a tertiary alicyclic hydrocarbon ester moiety, particularly a polycyclic ester such as methyladamantyl group, ethylfencyl group or a tricyclo decanyl moiety, particularly a polycyclic ester such as a methyladamantyl moiety, ethylfencyl moiety or a tricyclo decanyl moiety. References herein to a "tertiary alicyclic ester group" or other similar term indicate that a tertiary alicyclic ring carbon is covalently linked to the ester oxygen, i.e. —C(=O)O-TR where T is a tertiary ring carbon of alicyclic group R. In at least many cases, preferably a tertiary ring carbon of the alicyclic moiety will be covalently linked to the ester oxygen, such as exemplified by the below depicted specifically preferred polymers. However, the tertiary carbon linked to the ester oxygen also can be exocyclic to the alicyclic ring, typically where the alicyclic ring is one of the substituents of the exocyclic tertiary carbon (see for instance the substituted cyclohexyl group below having a molecular volume of 161 Å$^3$). Typically, the tertiary carbon linked to the ester oxygen will be substituted by the alicyclic ring itself, and/or one, two or three alkyl groups having 1 to about 12 carbons, more typically 1 to about 8 carbons, even more typically 1, 2, 3 or 4 carbons. The alicyclic group also will not contain aromatic substitution. The alicyclic groups may be suitably monocyclic, or polycyclic, particularly bicyclic or tyricyclic groups.

Preferably, the polymer contains from about 20 to 50 mole percent of nitrile units 1), and from about 30 to 60 mole percent of acid labile groups with alicyclic (preferably bridged bicyclic or other cage group), units 2), based on total units of the polymer. It is often preferred that the polymer contains 20 to 40 mole percent of nitrile units 1), or more particularly 20 to 38, 35, 34, 32 or 30 mole percent of nitrile units, based on total units of the polymer, and from 30 to 55, 50, 45 or 40 mole percent of alicyclic acid labile ester groups, based on total units of the polymer. Particularly preferred are polymers that contain 25, 26, 27, 28, 29, 30, 31, 32, 33, 34, 35, 36, 37, 38, or 39 mole percent of nitrile units 1) based on total units of the polymer; and 30, 31, 32, 33, 34, 35, 36, 37, 38, 39 or 40 mole percent of alicyclic acid labile groups 2) based on total units of the polymer.

Preferred polymers include those of the following Formula I:

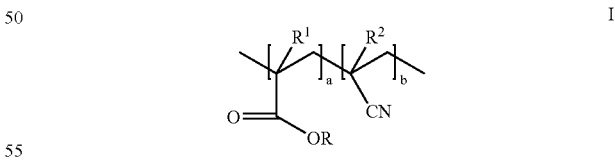

wherein R is a tertiary alicyclic group such as optionally alkyl adamantyl, optionally substituted alkyl fenchyl, optionally substituted tricyclo decanyl, or optionally substituted pinanyl;

$R^1$ and $R^2$ are each independently hydrogen or optionally substituted alkyl such as $C_{1-6}$ alkyl, and preferably $R^1$ and $R^2$ are each independently hydrogen or methyl;

a is the mole percent of the depicted alicyclic photoacid labile ester groups and is preferably 30 to 60 mole percent based on total polymer units, or other preferred value as discussed above; and b is the mole percent of the depicted nitrile groups and is preferably 20 to 50 mole percent based on total polymer units, or other preferred value as discussed above.

As discussed above, polymers of the invention may contain additional units, including acid groups and photoacid labile groups, such as polymers of the following Formula II:

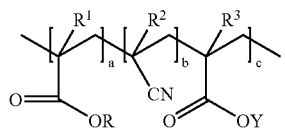
II wherein R, $R^1$ and $R^2$ are the same as defined above for Formula I;

$R^3$ is the same as defined for $R^1$ and $R^2$ above;

Y is hydrogen (forming a pendant acid such as by reaction of methacrylic or acrylic acid); optionally substituted alkyl, particularly alkyl having 3 to about 20 carbons and branched at the position linked to the carboxyl oxygen, such as tert-butyl, or an alicyclic groups such as optionally substituted adamantyl, fenchyl, isobornyl, tricyclo decanyl, or pinanyl; or optionally substituted alkoxy, particularly alkoxy having 3 to about 20 carbon atoms and 1, 2 or 3 alkoxy oxygen atoms, such as may be provided by reaction of ethoxyethyl methacrylate, ethoxyethyl acrylate, t-butoxy methacrylate, t-butylacrylate and the like;

a and b are the same as defined for Formula I above; and c is the mole percent of the acid or ester units that contain the Y moiety, and c will be greater than 0 and up to about 50 mole percent, more preferably from about 1, 2, 3, 4, or 5 mole percent to about 10, 15, 20, 25, 30, 35, 40, 45, or 50 mole percent, based on total units of the polymer.

Additional preferred polymers of the invention include those that contain dissolution enhancer units, such as anhydride or lactone repeat units. More particularly, polymers of the following Formula III are preferred:

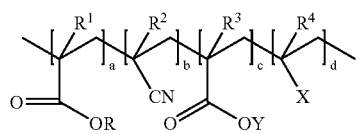
III wherein R, $R^1$, $R^2$, $R^3$, Y, a and b are the same as defined above for Formula II;

X is an anhydride or lactone, such as may be provide by reaction of itaconic anhydride, alpha-butyrolactone methacrylate, tetrahydro-2-oxo-2-H-furan-4-yl methacrylate and the like; $R^4$ is the same as defined for $R^1$ and $R^2$ above;

c is from 0 (where the ester with Y moiety is not present) to about 49 mole percent, more preferably from 0, 1, 2, 3, 4, or 5 mole percent to about 10, 15, 20, 25, 30, 35, 40, 45, or 50 mole percent, based on total units of the polymer;

d is the mole percent of the anhydride or lactone units X, and d will be greater than 0 and up to about 50 mole percent, more preferably from about 1, 2, 3, 4, or 5 mole percent to about 10, 15, 20, 25, 30, 35, 40, 45, or 50 mole percent, based on total units of the polymer.

Particularly preferred polymers of Formula III are those that contain lactone units, such as polymers of the following Formula IIIA:

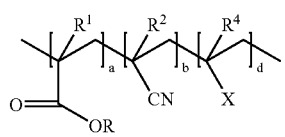
IIIA wherein R, $R^1$, $R^2$, $R^4$, a, b and d are the same as defined above for Formulae II and III;

X is a lactone group such as may be provided by reaction of alpha-butyrolactone methacrylate, tetrahydro-2-oxo-2-H-furan-4-yl methacrylate and the like.

Preferred alicyclic moieties of photoacid labile ester groups of polymers of the invention have rather large volume. It has been found that such bulky alicyclic groups can provide enhanced resolution when used in copolymers of the invention.

More particularly, preferred alicyclic groups of photoacid labile ester groups will have a molecular volume of at least about 125 or about 130 Å$^3$, more preferably a molecular volume of at least about 135, 140, 150, 155, 160, 165, 170, 175, 180, 185, 190, 195, or 200 Å$^3$. Alicyclic groups larger than about 220 or 250 Å$^3$ may be less preferred, in at least some applications. References herein to molecular volumes designate volumetric size as determined by standard computer modeling, which provides optimized chemical bond lengths and angles. A preferred computer program for determining molecular volume as referred to herein is Alchemy 2000, available from Tripos. For a further discussion of computer-based determination of molecular size, see T Omote et al, *Polymers for Advanced Technologies*, volume 4, pp. 277–287.

Some specifically preferred alicyclic groups of acid labile esters of the invention are shown immediately below together with the ester oxygen linkage, and with volumetric size values (Å$^3$) listed to the right of the alicyclic group.

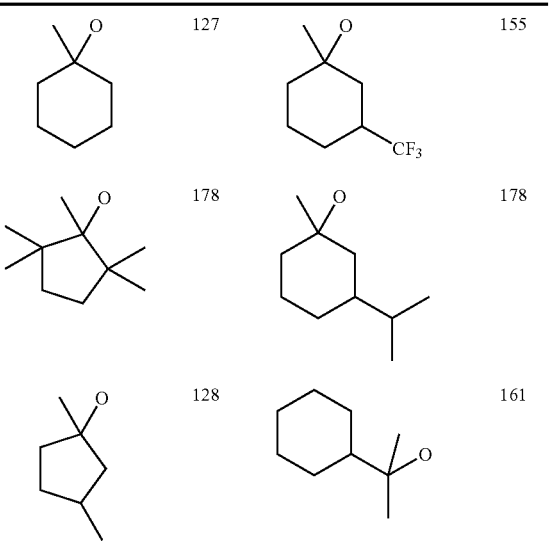

-continued

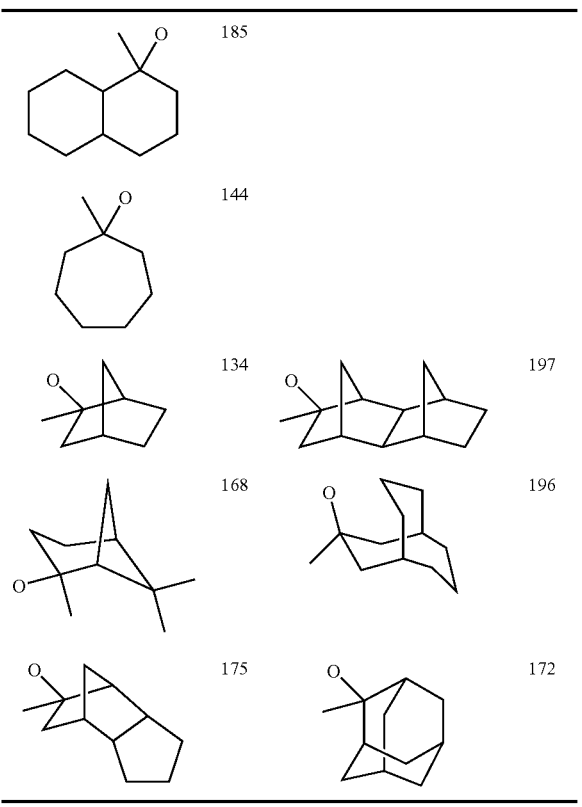

Specifically preferred polymers of the invention include the following terpolymers and tetrapolymers.

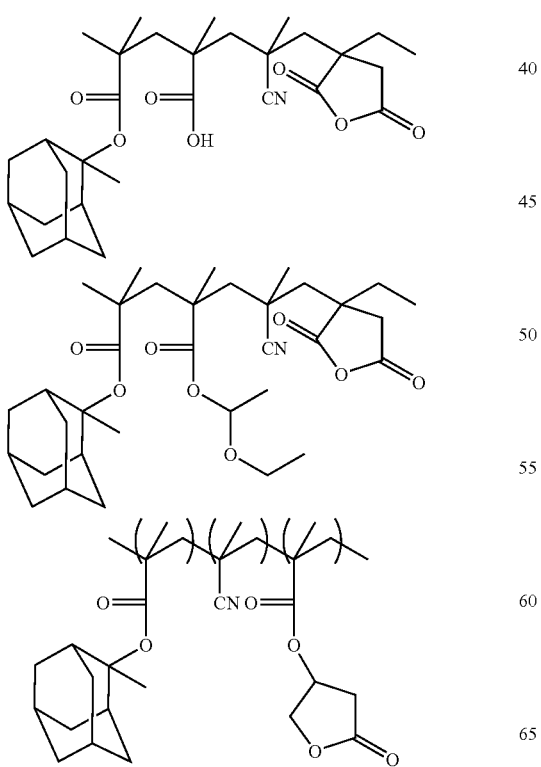

Polymers of the invention can be prepared by a variety of methods. One suitable method is an addition reaction which may include free radical polymerization, e.g., by reaction of selected monomers to provide the various units as discussed above in the presence of a radical initiator under an inert atmosphere (e.g., $N_2$ or argon) and at elevated temperatures such as about 70° C. or greater, although reaction temperatures may vary depending on the reactivity of the particular reagents employed and the boiling point of the reaction solvent (if a solvent is employed). Suitable reaction solvents include e.g. tetrahydrofuran, ethyl lactate and the like. Suitable reaction temperatures for any particular system can be readily determined empirically by those skilled in the art based on the present disclosure. A variety of free radical initiators may be employed For example, azo compounds may be employed such as azo-bis-2,4-dimethylpentanenitrile. Peroxides, peresters, peracids and persulfates also could be employed.

As discussed above, the invention also include novel compounds that are useful to prepare polymers of the invention, particularly ethylfenchol methacrylate and ethylfenchol acrylate of the following structure:

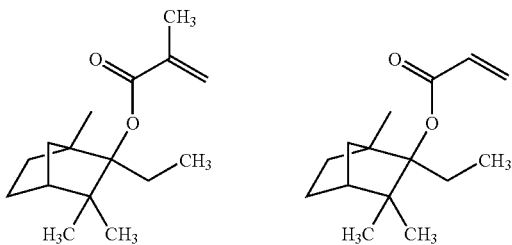

Those above fenchyl compounds can be synthesized by reaction of ethylfenchol under basic conditions, preferably in the presence of a strong base such as BuLi or other alkyllithium reagent, with a reactive acroyl or methacroyl compound, preferably the acid halide thereof such as methacryolyl chloride (to provide ethylfenchol methacrylate) or acryolyl chloride (to provide ethylfenchol acrylate). The reaction is preferably conducted in a suitable non-protic solvent such as tetrahydrofuran. See Example 1 which follows for exemplary preferred conditions.

Other monomers that can be reacted to provide a polymer of the invention can be identified by those skilled in the art. For example, to provide units of Formula I, suitable monomers include e.g. methacrylate or acrylate that contains the appropriate R group substitution on the carboxy oxygen of the ester group. Itaconic anhydride is another preferred reagent, preferably purified such as by extraction with chloroform. Vinyl lactones are also preferred reagents, such as alpha-butyrolactone. See the examples which follow for disclosure of suitable syntheses of monomers useful in preparation of polymers of the invention.

As discussed, various moieties may be optionally substituted, including groups of Formulae I, II, III and IIIA. A "substituted" substituent may be substituted at one or more available positions, typically 1, 2, or 3 positions by one or more suitable groups such as e.g. halogen (particularly F, Cl or Br); $C_{1-8}$ alkyl; $C_{1-8}$ alkoxy; $C_{2-8}$ alkenyl; $C_{2-8}$ alkynyl; hydroxyl; alkanoyl such as a $C_{1-6}$ alkanoyl e.g. acyl and the like; etc Preferably a polymer of the invention will have a weight average molecular weight (Mw) of about 800 or 1,000 to about 100,000, more preferably about 2,000 to about 30,000, still more preferably from about 2,000 to 15,000 or 20,000, with a molecular weight distribution (Mw/Mn) of about 3 or less, more preferably a molecular weight distribution of about 2 or less. Molecular weights (either Mw or Mn) of the polymers of the invention are suitably determined by gel permeation chromatography.

Polymers of the invention used in photoresist formulations should contain a sufficient amount of photogenerated acid labile ester groups to enable formation of resist relief images as desired. For instance, suitable amount of such acid labile ester groups will be at least 1 mole percent of total units of the polymer, more preferably about 2 to 50 mole percent, still more typically about 3 to 30 or 40 mole percent of total polymer units. See the examples which follow for exemplary preferred polymers.

As discussed above, the polymers of the invention are highly useful as a resin binder component in photoresist compositions, particularly chemically-amplified positive resists. Photoresists of the invention in general comprise a photoactive component and a resin binder component that comprises a polymer as described above.

The resin binder component should be used in an amount sufficient to render a coating layer of the resist developable with an aqueous alkaline developer.

The resist compositions of the invention also comprise a photoacid generator (i.e. "PAG") that is suitably employed in an amount sufficient to generate a latent image in a coating-layer of the resist upon exposure to activating radiation. Preferred PAGs for imaging at 193 nm and 248 nm imaging include imidosulfonates such as compounds of the following formula:

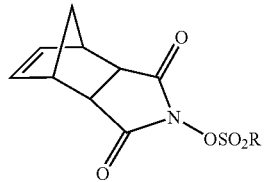

wherein R is camphor, adamantane, alkyl (e.g. $C_{1-12}$ alkyl) and perfluoroalkyl such as perfluoro($C_{1-12}$ alkyl), particularly perfluorooctanesulfonate, perfluorononanesulfonate and the like. A specifically preferred PAG is N-[(perfluorooctanesulfonyl)oxy]-5-norbornene-2,3-dicarboximide.

Sulfonate compounds are also suitable PAGs, particularly sulfonate salts. Two suitable agents for 193 nm and 248 nm imaging are the following PAGS 1 and 2:

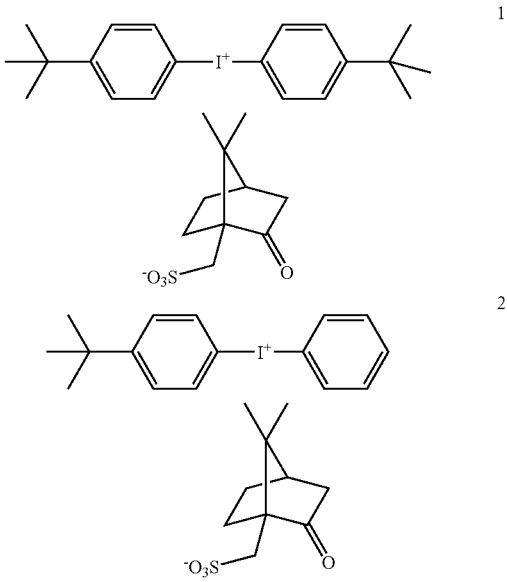

Such sulfonate compounds can be prepared as disclosed in European Patent Application 96118111.2 (publication number 0783136), which details the synthesis of above PAG 1.

Also suitable are the above two iodonium compounds complexed with anions other than the above-depicted camphorsulfonate groups. In particular, preferred anions include those of the formula $RSO_3-$ where R is adamantane, alkyl (e.g. $C_{1-12}$ alkyl) and perfluoroalkyl such as perfluoro ($C_{1-12}$ alkyl), particularly perfluorooctanesulfonate, perfluorobutanesulfonate and the like.

Other known PAGS also may be employed in the resists of the invention. Particularly for 193 nm imaging, generally preferred are PAGS that do not contain aromatic groups, such as the above-mentioned imidosulfonates, in order to provide enhanced transparency.

A preferred optional additive of resists of the invention is an added base, particularly tetrabutylammonium hydroxide (TBAH), or tetrabutylammonium lactate, which can enhance resolution of a developed resist relief image. For resists imaged at 193 nm, a preferred added base is a hindered amine such as diazabicyclo undecene or diazabicyclononene. The added base is suitably used in relatively small amounts, e.g. about 0.03 to 5 percent by weight relative to the total solids.

Photoresists of the invention also may contain other optional materials. For example, other optional additives include anti-striation agents, plasticizers, speed enhancers, etc. Such optional additives typically will be present in minor concentrations in a photoresist composition except for fillers and dyes which may be present in relatively large concentrations, e.g., in amounts of from about 5 to 30 percent by weight of the total weight of a resist's dry components.

The resists of the invention can be readily prepared by those skilled in the art. For example, a photoresist composition of the invention can be prepared by dissolving the components of the photoresist in a suitable solvent such as, for example, ethyl lactate, ethylene glycol monomethyl ether, ethylene glycol monomethyl ether acetate, propylene glycol monomethyl ether; propylene glycol monomethyl ether acetate and 3-ethoxyethyl propionate. Typically, the solids content of the composition varies between about 5 and 35 percent by weight of the total weight of the photoresist composition. The resin binder and photoactive components should be present in amounts sufficient to provide a film coating layer and formation of good quality latent and relief images. See the examples which follow for exemplary preferred amounts of resist components.

The compositions of the invention are used in accordance with generally known procedures. The liquid coating compositions of the invention are applied to a substrate such as by spinning, dipping, roller coating or other conventional coating technique. When spin coating, the solids content of the coating solution can be adjusted to provide a desired film thickness based upon the specific spinning equipment utilized, the viscosity of the solution, the speed of the spinner and the amount of time allowed for spinning.

The resist compositions of the invention are suitably applied to substrates conventionally used in processes involving coating with photoresists. For example, the composition may be applied over silicon wafers or silicon wafers coated with silicon dioxide for the production of microprocessors and other integrated circuit components. Aluminum-aluminum oxide, gallium arsenide, ceramic, quartz, copper, glass substrates and the like are also suitably employed.

Following coating of the photoresist onto a surface, it is dried by heating to remove the solvent until preferably the photoresist coating is tack free. Thereafter, it is imaged through a mask in conventional manner. The exposure is sufficient to effectively activate the photoactive component of the photoresist system to produce a patterned image in the resist coating layer and, more specifically, the exposure energy typically ranges from about 1 to 100 $mJ/cm^2$, dependent upon the exposure tool and the components of the photoresist composition.

As discussed above, coating layers of the resist compositions of the invention are preferably photoactivated by a short exposure wavelength, particularly a sub-300 and sub-200 nm exposure wavelength. As discussed above, 193 nm is a particularly preferred exposure wavelength. However, the resist compositions of the invention also may be suitably imaged at higher wavelengths. For example, a resin of the invention can be formulated with an appropriate PAG and used as a chemically-amplified positive I-line resist, i.e. a resist imaged at about 248 nm or 365 nm.

Following exposure, the film layer of the composition is preferably baked at temperatures ranging from about 70° C. to about 160° C. Thereafter, the film is developed. The exposed resist film is rendered positive working by employing a polar developer, preferably an aqueous based developer such as quaternary ammonium hydroxide solutions such as a tetra-allyl ammonium hydroxide solution; various amine solutions preferably a 0.26 N tetraethylammonium hydroxide, such as ethyl amine, n-propyl amine, diethyl amine, di-n-propyl amine, triethyl amine, or methyldiethyl amine; alcohol amines such as diethanol amine or triethanol amine; cyclic amines such as pyrrole, pyridine, etc. In general, development is in accordance with procedures recognized in the art.

Following development of the photoresist coating over the substrate, the developed substrate may be selectively processed on those areas bared of resist, for example by chemically etching or plating substrate areas bared of resist in accordance with procedures known in the art. For the manufacture of microelectronic substrates, e.g., the manufacture of silicon dioxide wafers, suitable etchants include a gas etchant, e.g. a halogen plasma etchant such as a chlorine or fluorine-based etchant such a $Cl_2$ or $CF_4/CHF_3$ etchant applied as a plasma stream. After such processing, resist may be removed from the processed substrate using known stripping procedures.

As discussed above, polymers and resists of the invention are highly resistant to plasma etchants, nothwithstanding the substantial or complete absence of aromatic content in the polymers.

More specifically, preferred polymers of the invention will exhibit good resistance to plasma etchants in the following plasma etch assay: 1) a solution of the test polymer is coated onto a silicon wafer and the solvent removed by heating to provide a polymer coating layer; 2) the thickness of the polymer coating measured; 3) the polymer coating layer exposed to a plasma chloride halide etchant under the following conditions: 150 sccm HBr, 50 sccm $Cl_2$, 65° C. chuck for 60 seconds of exposure to etchant; and 4) thickness of the polymer coating layer measured again after the etchant treatment. References herein to a "standard plasma etch assay" designate that protocol of steps 1) through 4). See also the Examples which follow, which also disclose that assay.

Particularly preferred polymers of the invention will exhibit an etch rate in such a standard plasma etch assay of no more than about 30 angstroms per second exposure to the plasma etchant, more preferably an etch rate of no more than about 25 angstroms per second exposure to the plasma etchant, and still more preferably an etch rate of no more than about 24, 23, 22, 21 or 20 angstroms per second exposure to the plasma etchant in such a standard plasma etch assay. Especially preferred polymers of the invention exhibit an etch rate of no more than about 20, 19, 18, 17, 16, 15 or even 14 angstroms per second exposure to the plasma etchant in such a standard plasma etch assay.

All documents mentioned herein are incorporated herein by reference. The following non-limiting examples are illustrative of the invention.

EXAMPLES 1–6

Syntheses of Cage and Lactone Monomers

EXAMPLE 1

Synthesis of Ethyl Fenchol Methacrylate

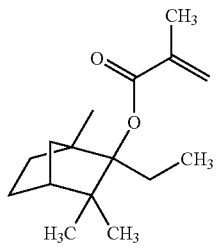

Materials Used

|  | Amount Charged | moles | Source |
|---|---|---|---|
| Ethyl fenchol | 182.31 g | 1.00 | Aldrich |
| n-BuLi (2.5 M in hexanes) | 440 mL | 1.10 | Aldrich |
| Methacryloyl chloride | 112.4 mL | 1.15 | Aldrich, distilled before use |
| THF anhydrous | 600 mL |  | Aldrich, degassed before use |

Procedure

All reaction glassware and needles were dried and flushed with dry $N_2$ before use and the reaction was carried out under nitrogen atmosphere.

1) Into a 2 L 3-neck RBF equipped with an addition funnel and a magnetic stirrer were added 182.31 g of 2-Ethyl fenchol and 600 mL of anhydrous THF. The resulting colorless solution was cooled with an ice-water bath.
2) A n-BuLi solution (440 mL) was transferred to the addition funnel via a double-tipped needle and then added to the cooled THF solution over 30 min. When added, the resulting yellowish solution was kept in the ice-water bath and stirred for 2 h.
3) Methacryloyl chloride (112.4 mL, 104.54 g) was added dropwisely over 20 min. The resulting yellow suspension was allowed to warm to room temperature and stirred overnight.
4) The LiCl salts were filtered off. The filtrate was cooled in an ice-water bath while 200 mL of pre-cooled DI water was added. The resulting solution was stirred for 1.5 h and the organic phase was isolated (some ether or THF may be added to assist extraction), washed with DI water (2×200 mL), then saturated $Na_2CO_3$ solution (2×200 mL), then DI water (3×200 mL) again, and dried over anhydrous $MgSO_4$.
5) The slightly yellow solution was concentrated on a rotary evaporator (bath temperature kept below 35°) to yield a clear slightly yellow liquid product. Yield >90%.
6) The crude EFMA may be purified to remove the yellow color plus methacrylic anhydride impurity via flash filtration through preconditioned silica (using hexanes) in Buchner. The monomer is eluted with hexanes only and comes through in the early eluting fractions as a colorless liquid when rotovapped. The product was judged pure by NMR.

EXAMPLE 2

2-Methyl-2-adamantyl Methacrylate

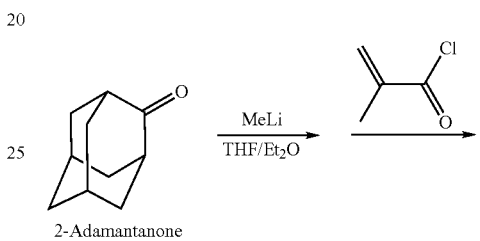

2-Adamantanone

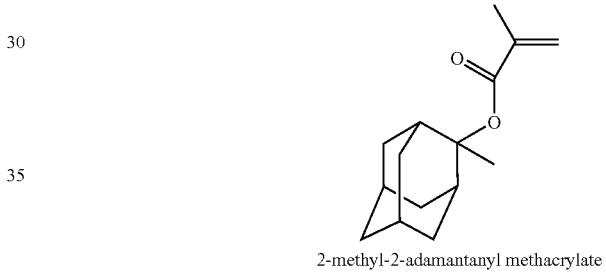

2-methyl-2-adamantanyl methacrylate (MAMA)

Material Used:

|  | Amount Charged | moles | Source |
|---|---|---|---|
| 2-Adamantanone | 150.22 g | 1.00 | Lancaster |
| MeLi (1.4 M in Ether) | 786 mL | 1.10 | Aldrich |
| Methacryloyl chloride | 112.4 mL | 1.15 | Aldrich, distilled before use |
| THF anhydrous | 600 mL |  | Aldrich, degassed before use |

Procedure

All reaction glassware and needles were dried and flushed with dry $N_2$ before use and the reaction was carried out under nitrogen atmosphere.

1) A Methyllithium solution (786 mL) was transferred via a double-tipped needle to a 2 L 3-neck RBF equipped with an addition funnel and a magnetic stirrer, and cooled with an ice-water bath.
2) 2-Adamantanone (150.22 g) was dissolved (over 0.5 h) in anhydrous THF (600 mL) and the resulting colorless solution was transferred to the addition funnel via a double-tipped needle and then added to the cooled MeLi solution over 30 min. When added, the resulting white suspension was allowed to warm to room temperature and stirred for 2 h.

3) The white suspension then was cooled using an ice-water bath and methacryloyl chloride (112.4 mL, 104.54 g) was added dropwisely over 20 min. The white solid faded out and a new white (LiCl) suspension formed. The resulting white suspension was allowed to warm to room temperature and stirred overnight.

4) The LiCl salts were filtered off. The filtrate was cooled in an ice-water bath while 200 mL of pre-cooled DI water was added. The resulting solution was stirred for 1.5 h and the organic phase was isolated (some ether or THF may be added to assist extraction), washed with DI water (2×200 mL), then saturated $Na_2CO_3$ solution (2×200 mL), then DI water (3×200 mL) again, and dried over anhydrous $MgSO_4$.

5) The slightly yellow solution was concentrated on a rotary evaporator (bath temperature kept below 35°) to yield a clear slightly yellow liquid product. Yield >90%.

6) The crude MAMA may be purified to remove the yellow color plus methacrylic anhydride impurity via flash filtration through preconditioned silica (using hexanes) in Buchner. The monomer is eluted with hexanes only and comes through in the early eluting fractions as a colorless liquid when rotovapped. The product was judged pure by NMR.

EXAMPLE 3

Synthesis of 8-methyltricyclodecanyl Methacrylate

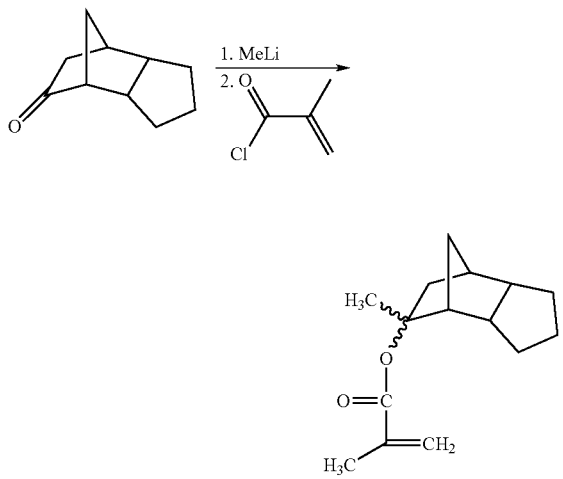

A solution of 125 ml of 1.4 M methyl lithium (in ethyl ether)in 100 ml of hexane was decanted into a three neck round-bottom flask at an ice-water bath. To it, a solution of 24.00 g of tricyclo[5.2.1.0]decan-8-one in hexane was added dropwise. After addition, the reaction mixture was stirred for 4 hours at 0° C. Then, a solution of 16 ml of methacroyl chloride in 100 ml of hexane was added dropwise at 0° C. After addition, the reaction mixture was stirred at the same bath for overnight (16 hours). After filtering the white salts, the organic layer was washed with water three times (3×300 ml). Then, the washed organic layer was dried over anhydrous $MgSO_4$. The organic solvent was removed by a rotary pump to give the crude title monomer (23.5 g). The monomer was purified by a flash column chromatography (purity >98%, silica gel with hexane). $^1H$ NMR: 6.05 (1H), 5.50 (1H), 1.95 (3H), 1.65 (3H), 2.25–0.85 (14H).

EXAMPLE 4

Synthesis of Tetrahydro-2-oxo-2-H-furan-4-yl Methacrylate

The methacrylate monomer, tetrahydro-2-oxo-2-H-furan-4-yl methacrylate was synthesized in one step esterification from commercially available compound. A mixture of (S)-(−)-β-hydroxy-γ-butyrolactone (41.77 g, 0.419 mole) and triethylamine (45.32 g, 0.449 mole) in 100 mL of dry THF was placed in a three-neck round-bottom flask under a dry nitrogen atmosphere at an ice-water bath. To it, a solution of distilled metharcyloyl chloride (45 mL, 0.461 mole) in 200 ML of dry THF was added slowly (about 1 hour). During the addition, white precipitation (triethylamine salt) was observed in the reaction mixture. The reaction mixture was stirred over night (about 18 hour). The resultant mixture was filtered, and the filtrate was concentrated by a rotary pump. The concentrated mixture was added 500 mL of ethyl acetate and washed with water (2×500 mL) twice. The organic layer was dried with anhydrous $MgSO_4$ and concentrated by a rotary pump. The purification of the crude monomer by column chromatography (neutral aluminum oxide, 300 g, hexane, then hexane/EtoAc=1/1). The purity of the monomer is about 95% (by NMR) and 52% yield. $^1H$ NMR ($CDCl_3$, ppm): 6.20 (1H), 5.70 (1H), 5.55 & 4.95 (1H), 4.55 (dd, 1H), 4.4 (d, 1H), 2.90 (dd, 1H), 2.70 (d, 1H), 1.95 (3H). $^{13}C$ NMR ($CDCl_3$, ppm): 174.1, 166.5, 135.5, 126.8, 72.9, 70.0, 34.5, 17.9.

EXAMPLE 5

Alpha—Butyrolactone Methacrylate Synthesis

To a 250 ml 3N-RB flask fitted with a gas inlet, thermometer, overhead stirrer and a 125 ml pressure equalizing dropping funnel was added 26.5 g triethylamine. The triethylamine was cooled to 5° C. using a water/ice bath. Once the triethylamine was at 5° C. the methacrylic acid was added dropwise over a 20–25 min period. The mixture exothermed ~10 C. After the addition was complete the water/ice bath was removed. While the solution was stirring (20 min) the dropping funnel was removed and replaced with a clean 125 ml pressure equalizing dropping funnel. The bromolactone (41.25 g)/THF (62.5 ml) was added dropwise over a 30 min. The mixture warmed from ~18° C. to ~30° C. with a precipitate forming. The reaction was heated to 55° C. and held at 55° C. for 16 hrs using an oil bath/hot plate. After heating for 16 hrs the mixture was cooled to 20° C. using a water/ice bath. The solid (44.5 g) was removed by vacuum filtration. The filtrates were reduced under partial pressure at 33–34° C. The resulting dark amber/brown oil was diluted with 90 g of methylene chloride. This solution was slowly poured onto a plug of silica gel (180 g, Baker 40 um flash chromatography packing) which had been pre-conditioned with methylene chloride. The crude mixture was allowed to pass into the silica gel plug by gravity. Once the crude mixture had passed the surface of the silica gel plug a fresh portion of methylene chloride was slowly poured onto the plug. The methylene chloride was pulled through the silica gel plug using reduced pressure. Once the methylene chloride had passed the surface of the silica gel plug the vacuum was removed then the next portion of methylene chloride was slowly poured onto the plug. This procedure was followed until all the product was extracted. The total filtrate was 850 ml. [The product was detected by spotting an aliquot on a TLC plate then illuminating with short UV.] To the orange filtrate was added 36 g of activated charcoal. The mixture was stirred for 1.5 hrs then filtered through a Celite plug (pre-conditioned with methylene chloride). The charcoal/Celite was washed with (2×100 ml, 1×50 ml methylene chloride). The filtrate was then washed with 2×200 ml D.I. water. The layers were separated and the organic layer was dried over 100 g of sodium sulfate. The mixture was stirred for 15–30 min. The sodium sulfate was removed and washed with 2×50 ml methylene chloride. The pale yellow filtrate (1.2 L) was stripped under reduced pressure at 33–34° C. leaving 36.4 g of a pale orange oil, Yield 85.6%.

EXAMPLE 6

Synthesis of Pinanyl Methacrylate

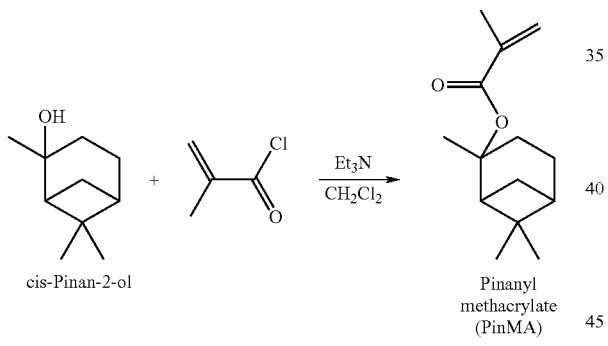

Materials Used

|  | Amount Charged | Moles | Source |
| --- | --- | --- | --- |
| cis-Pinan-2-ol | 15.43 g | 0.10 | Fluka |
| Et$_3$N | 12.14 g | 0.12 | Aldrich, distilled before use |
| Methacryloyl chloride | 13.07 g | 0.125 | Aldrich, distilled before use |
| CH$_2$Cl$_2$ | 230 mL |  | Aldrich, dried and distilled |

Procedure:

All reaction glassware and needles were dried and flushed with dry N$_2$ before use and the reaction was carried out under nitrogen atmosphere.

1) Into a 500 mL 3-neck round-bottom-flask equipped with an addition funnel and a magnetic stirrer were added 15.43 g of cis-pinan-2-ol and 200 mL of dry CH$_2$Cl$_2$ (Stirred over CaH$_2$ overnight, then distilled and stored over activated molecular sieves). The resulting colorless solution was cooled with an ice-water bath.
2) Triethylamine (12.14 g) was added through the addition funnel to the cooled CH$_2$Cl$_2$ solution over 10 min. After added, the resulting solution was kept in a dry-ice/acetone bath (−67° C.).
3) A CH$_2$Cl$_2$ (30 mL) solution of methacryloyl chloride (13.07 g) was added dropwisely over 20 min. The resulting orangish suspension was allowed to warm to room temperature and stirred for 2 h.
4) The chloride salts were filtered off. The filtrate was washed with saturated Na$_2$CO$_3$ solution (2×200 mL), then DI water (3×200 mL), and dried over anhydrous MgSO$_4$.
5) The slightly yellow CH$_2$Cl$_2$ solution was concentrated on a rotary evaporator (bath temperature kept below 35°) to yield a clear slightly yellow liquid product. Yield=79%. The product was judged pure by NMR.

EXAMPLE 7–8

Syntheses of Polymers of the Invention

EXAMPLE 7

Tetrapolymer Methyladamantylmethacrylate/methylacrlic acid/methacrylonitrile/itaconic anhydride in Respective Molar Amounts of 38/7/34/21

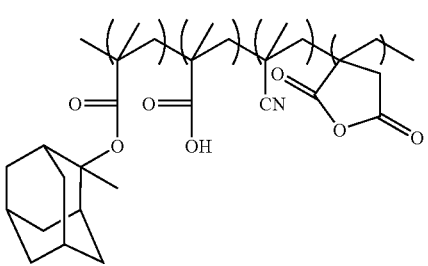

38/7/34/21

2-Methyladamantanyl methacrylate (31.89 g, 0.134 mol), methacrylic acid (2.13 g, 0.025 mol), methacrylonitrile (8.06 g, 0.120 mol), and itaconic anhydride (8.32 g, 0.074 mol) were dissolved in 30 mL of tetrahydrofuran. The resulting colorless solution was deoxygenated by gently bubbling a stream of N$_2$ through the stirring solution for 15 minutes, placed under N$_2$, and heated to 90° C. (oil bath temperature). VAZO67 (1.36 g, 0.0071 mol) dissolved in 7 ml of tetrahydrofuran, was then added to the refluxing mixture over 10 minutes. The polymerization was then refluxed with stirring for 4 hours, then diluted with an additional 94 mL of tetrahydrofuran (bringing the reaction mixture to 30% of solids) and cooled to room temperature. The polymer was isolated by precipitation into 1300 mL of hexanes, filtered, dried, re-dissolved in 130 mL of tetrahydrofuran, precipitated into 1300 mL of hexanes, filtered, washed well with hexanes, and dried in a vacuum oven at 40° C. for 24 hours. Yield 35 g (70% of theory). Composition of the title tetrapolymer was determined by quantitative C-13 NMR and was found to be within experimental error of the monomer feed ratio. Mw =13,189, Mn=7799 and polydispersity=1.69. Glass transition temperature=157° C.

EXAMPLE 8

Synthesis of Terpolymer of 2-methyladamantanyl-methacrylate/methacrylonitrile/alpha-butyrolactone Methacrylate in Respective Molar Amounts of 40/30/30.

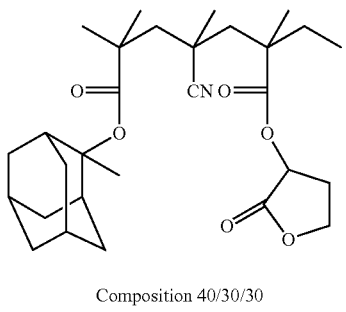

Composition 40/30/30

2-Methyladamantanyl methacrylate (14.21 g, 0.061 mol), methacrylonitrile (3.05 g, 0.045 mol), and alpha-butyrolactone methacrylate (7.74 g, 0.045 mol) were dissolved in 66 mL of tetrahydrofuran. The resulting colorless solution was deoxygenated by gently bubbling a stream of $N_2$ through the stirring solution for 15 minutes, placed under $N_2$, and heated to 90° C. (oil bath temperature). VAZO67 (0.58 g, 0.0030 mol) dissolved in 7 ml of tetrahydrofuran, was then added to the refluxing mixture over 10 minutes. The polymerization was then refluxed with stirring for 20 hours and cooled to room temperature. The polymer was isolated by precipitation into 800 mL of hexanes, filtered, dried, re-dissolved in 70 mL of tetrahydrofuran, precipitated into 800 mL of hexanes, filtered, washed well with hexanes, and dried in a vacuum oven at 40° C. for 24 hours. Yield 19.8 g (79% of theory). Composition of the title terpolymer was determined by quantitative C-13 NMR and was found to be within experimental error of the monomer feed ratio.

EXAMPLE 9

Etch Resistance of Polymers of the Invention

Additional polymers of the invention were prepared by the general procedures of Examples 7 and 8 above and tested for resistance to plasma etchant. The polymer structures and etch resistance values are set forth immediately below. A comparative phenolic polymer (last depicted polymer) was also tested. References to "Composition" below with subsequent values designate the molar percent of depicted copolymer units, from left to right in the structural depiction. Hence, the immediately following Composition (1) is a polymer that has 35 mole percent of the photoacid-labile adamantyl ester groups; 14 mole percent of the acid groups; 28 mole percent of the nitrile groups; and 23 mole percent of the anhydride groups.

The etch resistance test process was as follows, 150 sccm HBr, 50 sccm Cl2, 65° C. chuck, 300 W. The experiment was carried out on a LAM TCP etcher at International SEMATECH. Two wafers of each sample (polymer in ethyl lactate solvent) were coated on silicon wafers followed by heating at 130° C. to remove solvent, the thickness of each wafer was measured after coating and then again after being etched for 60 seconds. The thickness change was then calculated to give an etch rate tabulated as Å/s.

| Composition | Etch (Å/sec) |
|---|---|
| 35/14/28/23 (1) | 14.5 |
| 35/14/28/23 (2) | 13.1 |
| 36/7/35/22 (3) | 13.9 |
| 25/28/10/14/23 (4) | 20.5 |
| 80/20 (5) | 14.8 |

As can be seen from the above data, compositions containing a cage monomer content of 30 to 60 mol % in conjuction with 20 to 60 mol % nitrile monomer, structures (1), (2) and (3), exhibit approximately 25% better etch resistance (15 Å/sec) than methacrylate compositions out with this range of cage monomer and nitrile content. For example, comparative structure (4) which contains a molar ratio of cage monomer below 30 mol % in combination with nitrile content below 20 mol %, results in an etch rate of 20.5 Å/sec. It should also be noted that the etch resistance of these high cage and nitrile containing methacrylate polymers (1), (2) and (3) is equivalent to typical phenolic based polymer compositions used in 248 nm resists, structure (5).

EXAMPLE 10

Preparation of Photoresists of the Invention and Lithographic Testing of Same

Examples of Formulations for Etch Testing

| Polymer | Monomers | Monomer Ratios | Formula Type |
|---|---|---|---|
| (1) | 35:14:28:23 | MAMA:MAA:MAN:ITA | 1 |
| (1) | 35:14:28:23 | MAMA:MAA:MAN:ITA | 2 |
| (2) | 35:14:28:23 | MAMA:EEMA:MAN:ITA | 1 |
| (3) | 36:7:35:22 | MAMA:EEMA:MAN:ITA | 1 |

Formulation Type
1. This type of formulation comprised of 16.5% solids dissolved in a 2:1 blend of 2-Heptanone:Propylene glycol methyl ether acetate. The solids in the formulation were 90.2% of the polymer noted above, 0.1% of a surface leveling agent, 0.063% of a base additive and two photo acid generating species one at level of 9.0% the other at a level of 0.6%.
2. This type of formulation comprised of 16.5% solids dissolved in a 2:1 blend of 2-Heptanone:Propylene glycol methyl ether acetate. The solids in the formulation were 96.7% of the polymer noted above, 0.1% of a surface leveling agent, 0.063% of a base additive and two photo acid generating species one at level of 2.5% the other at a level of 0.6%.

A series of polymers having the composition given in the table above (formulated as noted) were tested for etch resistance. The etch process was as follows, 150 sccm HBr, 50 sccm $Cl_2$, 65° C. chuck, 300 W. The experiment was carried out on a LAM TCP etcher at International SEMATECH. Two wafers of each sample were coated on silicon wafers at 130° C., the thickness of each wafer was measured after coating and then again after being etched for 60 seconds. The thickness change was then calculated to give an etch rate tabulated as Å/s. The data is given in the Table above. Also given are the etch rates of a standard 248 nm resist (5) and another experimental 193 nm resist system (4). Relative to these resists the new polymers show improved etch resistance if one considers the relative ohnishi parameter of the samples. The new samples etch at slower rates than what would be expected using this parameter.

Polymers (1), (2) and (3) as well as exhibiting good etch resistance, equivalent to typical 248 nm resists, also showed excellent resolution capability using 193 nm exposure. 140 nm features were resolved by each of the resists that contained the three polymers.

The foregoing description of the invention is merely illustrative thereof, and it is understood that variations and modification can be made without departing from the spirit or scope of the invention as set forth in the following claims.

What is claimed is:

1. A method of forming a positive photoresist relief image, comprising:
   (a) applying a coating layer of a photoresist composition on a substrate,
   the photoresist composition comprising a photoactive component and a resin component that comprises a polymer that at least substantially free of aromatic groups and comprises 1) a photoacid-labile ester group that has an alicyclic moiety, and 2) a nitrile group; and
   (b) exposing the photoresist composition layer to patterned radiation and developing the exposed photoresist layer to yield a relief image.

2. The method of claim 1 wherein the polymer further comprises a lactone group.

3. The method of claim 1 wherein the photoresist layer is exposed to radiation having a wavelength of less than 200 nm.

4. The method of claim 1 wherein the photoresist layer is exposed to radiation having a wavelength of about 193 nm.

5. The method of claim 1 wherein the alicyclic moiety is a bicyclic group.

6. The method of claim 1 wherein the alicyclic moiety is a tricyclic group.

7. The method of claim 1 wherein after development the substrate is processed in areas bared of photoresist.

8. A method of forming a positive photoresist relief image, comprising:
   (a) applying a coating layer of a photoresist composition on a substrate,
   the photoresist composition comprising a photoactive component and a resin component that comprises a polymer that at least substantially free of aromatic groups and comprises 1) a photoacid-labile ester group that has an alicyclic moiety, the ester group present in an amount of from about 30 to 60 mole percent based on total units of the polymer, and 2) a nitrile group present in an amount of from about 20 to 50 mole percent based on total units of the polymer; and
   (b) exposing the photoresist composition layer to patterned radiation and developing the exposed photoresist layer to yield a relief image.

9. The method of claim 8 wherein the polymer further comprises a lactone group.

10. The method of claim 8 wherein the photoresist layer is exposed to radiation having a wavelength of less than 200 nm.

11. The method of claim 8 wherein the photoresist layer is exposed to radiation having a wavelength of about 193 nm.

12. The method of claim 8 wherein the alicyclic moiety is a bicyclic group.

13. The method of claim 8 wherein the alicyclic moiety is a tricyclic group.

14. The method of claim 8 wherein after development the substrate is processed in areas bared of photoresist.

15. The method of claim 1 wherein the alicyclic moiety is an optionally substituted alkyl adamantly.

16. The method of claim 8 wherein the alicyclic moiety is an optionally substituted alkyl adamantly.

* * * * *